United States Patent [19]

Navarrini et al.

[11] Patent Number: 5,241,110
[45] Date of Patent: Aug. 31, 1993

[54] PROCESS FOR PREPARING PERFLUOROALKOXYSULPHONIC COMPOUNDS

[75] Inventors: Walter Navarrini; Vittorio Montanari; Anna M. Staccione, all of Milan, Italy

[73] Assignee: Ausimont S.P.A., Italy

[21] Appl. No.: 727,700

[22] Filed: Jul. 10, 1991

[30] Foreign Application Priority Data

Jul. 12, 1990 [IT] Italy ................... 20920 A/90

[51] Int. Cl.⁵ .................. C07C 303/02; C07C 303/18
[52] U.S. Cl. ................... 562/111; 562/825; 564/80; 564/82; 564/96
[58] Field of Search .............. 562/825, 111; 564/80, 564/82, 96

[56] References Cited

U.S. PATENT DOCUMENTS

| | | | |
|---|---|---|---|
| 4,180,639 | 12/1979 | Caporiccio et al. | 526/243 |
| 4,411,841 | 10/1983 | Geisler | 562/825 |
| 4,906,770 | 3/1990 | Marchionni et al. | 560/300 |
| 4,968,537 | 11/1990 | Lenti et al. | 427/393.6 |

FOREIGN PATENT DOCUMENTS 201871 11/1986 European Pat. Off. .

OTHER PUBLICATIONS

"1,1,2,2-Tetrafluoro-2-(polyfluoroalkoxy)ethanesulfonyl Fluorides", Ting-Ji Huang, et al., Inorganic Chemistry, vol. 26, No. 14, pp. 2604–2606, 1987.

Primary Examiner—José G. Dees
Assistant Examiner—Joseph M. Conrad
Attorney, Agent, or Firm—Morgan & Finnegan

[57] ABSTRACT

This invention relates to a process for preparing perfluoroalkoxysulphonic compounds having formula:

$$R_f(-OC_2F_4-SO_2X)_p \quad (I)$$

wherein $R_f$ represents a perfluoroalkyl or perfluoroethereal group, X represents F, OH or OM, in which M is an alkaline cation, an alkaline-earth cation, or X represents $NR_1R_2$, in which $R_1$ and $R_2$, independently of each other, represent H or an alkyl group containing from 1 to 5 carbon atoms and p is a number selected from 1 to 2, characterized in that the perfluoro vinyl sulphonyl fluoride of formula (II) $CF_2=CF-SO_2F$ is reacted with a hypofluorite of formula (III):

$$R_f(OF)_r \quad (III)$$

wherein $R_f$ is the same as defined above, and r represents 1 or 2, optionally in an inert solvent, at a temperature approximately ranging from $-140°$ C. to $+40°$ C., and in that, if so desired, from the compound of formula (I) so obtained in which X=F, the corresponding derivatives, in which X has the other meanings defined above, are obtained by means of conventional techniques.

6 Claims, No Drawings

PROCESS FOR PREPARING PERFLUOROALKOXYSULPHONIC COMPOUNDS

FIELD OF THE INVENTION

A few subclasses of compounds (I) are new per se. The derivatives are utilized as polymerization catalysts, surfactants and electrolytes in electric generators.

The present invention relates to a process for preparing perfluoroalkoxysulphonic compounds having the formula:

$$R_f(-OC_2F_4-SO_2X)_p \qquad (I)$$

wherein:

p represents 1 or 2;

X represents F, OH or OM, in which M represents an alkali or alkaline-earth metal cation, or X represents $NR_1R_2$ in which $R_1$ and $R_2$, independently of each other, represent H or an alkyl group containing from 1 to 5 carbon atoms;

$R_f$, for p=1, represents a perfluoroalkyl group containing from 1 to 6 carbon atoms or a perfluoroethereal chain having the formula:

$$R_3-O-(R_4O)_k-(CF)_q-CF_2-$$
$$\qquad\qquad\qquad\quad |$$
$$\qquad\qquad\qquad\quad D$$

wherein:

$R_3$ represents a perfluoroalkyl group containing from 1 to 3 carbon atoms;

$R_4O$ represents a perfluorooxyalkylene group selected from $$-CF_2O-, \ -CF_2CF_2O- \text{ and } -CF_2CFO-;$$
$$\qquad\qquad\qquad\qquad\qquad\qquad\quad |$$
$$\qquad\qquad\qquad\qquad\qquad\qquad\ CF_3$$

D represents —F or —$CF_3$;

k represents 0 or an integer from 1 to 100 included, and when k is equal to or higher than 2, at least two of the abovesaid perfluorooxyalkylene groups can be simultaneously present according to a random distribution of their combinations;

q represents 0 or 1; and for p=2, $R_f$ represents a perfluoroalkylene chain containing from 2 to 6 carbon atoms or a perfluoroethereal chain having the formula:

$$-(R_4O)_{k'}-(CF)_q-CF_2-$$
$$\qquad\qquad\quad |$$
$$\qquad\qquad\quad D$$

wherein $R_4O$, D and q are as defined hereinabove and k' represents an integer from 1 to 100.

Unit $(OC_2F_4-SO_2X)$ in formula (I) can appear in the isomeric forms:

$$-OCF-SO_2X$$
$$\ \ |$$
$$\ \ CF_3$$

and/or $-O-CF_2-CF_2-SO_2X$ and for p=2 they are separated by the $R_f$ group.

Thus, the compound of formula (I) can appear, for p=2, in the symmetric or asymmetric form. For example, in formula (I), structures of formula:

$$XSO_2-CF_2-CF_2-O-R_f-O-CF_2-CF_2-SO_2X \text{ or}$$

$$XSO_2-CF-O-R_f-O-CF_2-CF_2-SO_2X$$
$$\quad\ \ |$$
$$\quad\ \ CF_3$$

are contemplated.

Preferably $R_f$, when it represents a perfluoroalkyl or perfluoroalkylene group, contains from 1 to 3 carbon atoms; k and k' preferably represent an integer from 1 to 50.

A few classes of products defined hereinafter and comprised in the abovesaid formula (I) are new in themselves and represent a further aspect of the present invention.

The compounds so obtained represent products having interesting applicative properties in a wide range of industrial appliances. Therefore they can be utilized for example-as regards the obtained perfluorinated sulphonic acids-as acid catalysts in Friedel-Crafts reactions, in polymerization and isomerization reactions, and as antifoaming and surface active agents in general. Another utilization, for the compounds in which X=F, is the one as intermediates for the synthesis of the respective acid and amidic derivatives.

Furthermore, the saline derivatives (X=OM) or the amidic derivatives (X=$NR_1R_2$ where $R_1$ and $R_2$ are the same as already defined), namely the perfluoroalkylsulphonamides and the perfluoroalkylsulphonates, are surfactants exhibiting a high stability under drastic conditions, under which the common sulphonamides and hydrogenated salts cannot be utilized. Lastly, they can be utilized as electrolytes in electric generators.

BACKGROUND OF INVENTION

As far as the Applicant knows, no processes have been described so far, which are suitable for directly preparing polyfluorinated or perfluorinated derivatives of the ethereal type containing only the functionality of sulphonic nature, starting from compounds containing other reactive groups and/or functionalities, for example estereal, ethylenic etc. functionalities.

As is known, the simultaneous presence of other functionalities renders the product chemically less stable.

U.S. Pat. No. 2,732,398 describes a process for obtaining perfluoroalkylsulphonic derivatives, which are chemically inert, by direct electrochemical fluorination of alkylsulphonic acids.

Also the synthesis of polyfluoro-alkoxy fluorosulphonic compounds, containing hydrogen and/or halogens other than fluorine is known (see Inorganic Chem. 1987; 26; 2307; 2604).

However, these are processes which can neither lead to the preparation of the compounds forming the object of the present invention, nor give useful hints to this purpose.

In particular the process described in U.S. Pat. No. 2,732,398 leads only to the obtainment of perfluoroalkyl sulphonic compounds and it cannot be applicated to the perfluoroalkoxysulphonic compounds forming the object of the present invention.

DETAILED DESCRIPTION OF THE INVENTION

Thus, it is an object of the present invention to provide a process for directly and selectively preparing, in a single step, the abovesaid perfluoroalkoxy sulphonic compounds.

Another object resides in providing new classes of perfluoroalkoxy sulphonic compounds, in the absence of other functional groups different from the sulphonic group and derivatives thereof.

These and still further objects, which will be more clearly apparent to those skilled in the art from the following description, are achieved, according to the present invention, by a process for preparing perfluoroalkoxy sulphonic compounds having the above-defined formula (I), characterized in that the perfluoro vinyl sulphonyl fluoride of formula (II):

$$CF_2=CF-SO_2F \qquad (II)$$

is reacted with a hypofluorite of formula (III):

$$R_f(OF)_r \qquad (III)$$

wherein:
$R_f$ has the meaning defined above, and
r represents 1 or 2,
optionally in an inert solvent, at a temperature ranging from $-140°$ C. to $+40°$ C. approximately, and in that, if so desired, from the compound of formula (I) so obtained, in which X=F, the corresponding derivatives, in which X=OH, OM or $NR_1R_2$ as defined before, are obtained by means of conventional techniques.

Defined more in detail, the process of the present invention comprises the reaction of perfluoro vinyl sulphonyl fluoride (II) with a mono- or bis-hypofluorite (III), optionally in an inert organic solvent, selected from the straight and cyclic fluorocarbons, chlorofluorocarbons, perfluoroamines and perfluorinated alkyl ethers.

Examples of fluorocarbons and chlorofluorocarbons suitable for the purpose are $CFCl_3$, $CF_2Cl_2$, $c.C_4F_8$, $c.C_6F_{12}$, 1-chloropentafluoroethane, 1,1,2-trichloro-1,2,2-trifluoroethane, 1,2-dichlorotetrafluoroethane and 1,1,1-trifluorotrichloroethane.

Examples of suitable perfluoroamines are the "Fluorinert" ®, perfluoroaminic products manufactured by 3M.

Examples of suitable perfluorinated ethers are the perfluoropolyethers having a boiling point lower than 250° C., such as "Galden" ® produced by Montefluos.

It is operated at a temperature ranging from $-140°$ to $+40°$ C., preferably from $-100°$ to $0°$ C.

Reagents (II) and (III) are utilized in at least substantially equimolar ratios, referred to the OF functionality which is present.

Nevertheless it is also possible to operate in the presence of an excess of reagent (II), for example according to the following molar ratio:
(Mols of (III)×r):(II)=about 1:3
wherein:
r=1 or 2.

When the starting hypofluorite (III) contains a perfluoroethereal chain, it can be in accordance, for example, with the following formula:

$$OF-CF_2-O-(CF_2CF_2O)_m(CF_2O)_n-CF_2-OF$$

in which m and n represent integers ranging from 1 to 100, with $m+n \leq 100$, and the perfluorooxyalkylene units are randomly distributed along the chain.

From the derived perfluoroalkoxysulphonic compound of formula (I) so obtained, in which X=F, the corresponding compounds, in which X=OH, OM or $NR_1R_2$, as defined before, can be respectively obtained as follows. For example the sodium salts can be obtained by hydrolizing the corresponding sulphonylfluorides in a solution of NaOH in water and methanol.

The acids are obtained, for example, by reacting the sodium salts with $H_2SO_4$ at 96% and by distilling the corresponding acid or, as an alternative, by causing an aqueous solution of the respective salt to flow over a cation exchange resin containing acid sulphonic groups.

The sulphonamides are preparable for example by directly reacting the sulphonyl fluorides with amines $NHR_1R_2$, in which $R_1$ and $R_2$ are the same as already defined before.

To carry out the reaction of the present invention, times ranging from 1 hour to 24 hours, approximately, are usually sufficient.

The separation of the compounds of formula (I) from the reaction mixture is conducted according to known techniques such as, for example, the distillation under vacuum, collecting the products in cooled traps, the chromatography, etc.

From the literature there are known methods of preparing hypofluorites of formula $R_f(OF)_r$ (III), where $R_f$ consists of a perfluoroalkyl or perfluoroalkylene radical; they are described for example in Russian Chemical Reviews, vol. 49, page 668, 1980.

Analogously, the hypofluorites of formula (III), in which $R_f$ consists of a perfluoroethereal residue as defined in formula (I), can be produced, they too, according to known techniques, for example conforming to the process described in European patent 308,905.

Perfluoro vinyl sulphonyl fluoride (II) is a compound easy to be prepared in one step only, by reacting for example a sulfone of perfluoropropene with an oxide or a carbonate of an element belonging for example to Groups III A and IV A per the Periodic Table, at a temperature from 150° to 450° C., recovering compound (II) from the reaction effluent by condensation, distillation, etc. (see European patent application 395.102).

Of course it is possible, for applicative purposes, not to proceed to the separation of the individual products, since the isomeric mixtures obtained from the compounds of formula (I) are directly utilizable as such, without the need of further purifications, etc.

The above-described process is particularly advantageous. In fact, according to the process of the present invention it is possible to obtain in a single step and with high yields, fully fluorinated compounds, free from other functional groups besides the desired sulphonic group.

This is surprising because, owing to the high oxidant properties of hypofluorites, it was expected that the reaction followed another course (in particular with the breakage of the $C-SO_2F$ bond) or gave rise to relevant quantities of by-products generated by secondary reactions. It is in fact known, e.g., that it is not possible to epoxidize $CF_2=CF-SO_2F$ and that its reation with strong oxidants, such as $CrO_3+HSO_3F$ gives rise to the breakage of the $C-SO_2F$ bond with the formation of a mixture of $COF_2$, $SO_2$ and $CO_2$ (see Farhad Forohar, Ph. D. Dissertation, "The Chemistry of Perfluoro Vinyl Sulphonyl Fluoride", Clemson University, United States, Clemson S. C. 29634/1905, 1990). We have, on the contrary, surprisingly found that the hypofluorites conforming with the present invention are capable of easily and selectively reacting only with the ethylene functionality of perfluorovinyl sulphonyl fluoride (II) without modifying the fluoro-sulphonic functionality.

Lastly, the process of the present invention is consistent with a continuously operating plant, as is described for example in European patent application EP-201871-what involves considerable economic and operative industrial advantages.

As mentioned hereinbefore, a few classes of products, comprised in the above-defined formula (I) and obtainable by means of the process of the present invention, are new in themselves and represent a further object of the present invention.

Said classes are the following classes of perfluoroalkoxysulphonic compounds which correspond to the following formulae:

A. $CF_3-OC_2F_4-SO_2X$;
B. $R'_f-OC_2F_4-SO_2-NR_1R_2$;
C. $R''_f(-OC_2F_4-SO_2X)_2$;
D. $R'''_f(-OC_2F_4-SO_2X)_p$;

in which formulae:
$R'_f$ represents a perfluoroalkyl group containing from 2 to 6 carbon atoms;
$R''_f$ represents a perfluoroalkylene group containing from 1 to 6 carbon atoms;
$R'''_f$ represents a perfluoroethereal group defined above as $R_f$, and symbols X, $R_1$, $R_2$ and p are the same as already defined.

Furthermore, groups $-OC_2F_4-SO_2X$ or $-OC_2F_4-SO_2-NR_1R_2$ can appear in the previously indicated isomeric forms.

The present invention will be now illustrated more in detail making reference to the examples given hereinafter, which are merely illustrative and therefore are not to be construed as to be a limitation of the invention.

EXAMPLES

In particular in the following examples-which were carried out discontinuously for experimental reasons-the transfer of the reagents was effected by condensing them in the reaction reactor at the temperature of liquid nitrogen, thereby avoiding also premature reactions during said transfer, and then by allowing the temperature to rise up to the indicated operative values.

EXAMPLE 1

Perfluoro-2-methoxyethylsulphonyl fluoride (1) and perfluoro-1-methoxyethylsulphonyl fluoride (2).

In a steel cylinder of 30 ml of volume there were condensed, at the temperature of liquid nitrogen, 8 mmols of perfluorovinylsulphonyl fluoride, 20 mmols of $CFCl_3$ as an inert solvent, and 8 mmols of $CF_3OF$.

The temperature was allowed to rise up to $+25°$ C. and, after this temperature had been maintained for 20 hours, the reaction rough product was distilled at a pressure of $10^{-3}$ torr, causing the vapors to pass through traps maintained at temperatures of $-60°$ C., $-80°$ C., $-110°$ C. and $-196°$ C.

The trap at $-60°$ C. contained high-boiling products.
The trap at $-80°$ C. contained 4.54 mmols of products which, by means of gas-chromatography combined with mass spectrometry, infrared spectroscopy and NMR, were identified as a mixture of perfluoro-2-methoxyethylsulphonyl fluoride (1) and perfluoro-1-methoxyethylsulphonyl fluoride (2) in a ratio (1):(2)=70:30 calculated from the areas of the corresponding gas-chromagraphic peaks and confirmed by the integration of the corresponding NMR signals.

The trap at $-110°$ C. contained 21.27 mmols of a mixture of $CFCl_3$ and products (1) and (2).
The trap at $-196°$ C. contained $COF_2$.

The conversion of perfluorovinylsulphonyl fluoride was complete. The yield, calculated as ratio between isolated mols of (1)+(2) and mols of the starting perfluorovinyl sulphonyl fluoride, was equal to 56%.

Products (1) and (2) were separable by means of preparative gas-chromatography: the retention times on a 3-meter column SP 1000, using helium as a carrier gas, were as follows:
check $CFCl_3 = 100$; (1)=80; (2)=59.

Characterization of products (1) and (2)

Gas-chromatography (column SP 1000, 60°-200° C., 7° C./minute): retention times as compared with the check:
$CFCl_3 = 100$: (1)=80, (2)=59.

Mass spectra (electronic impact): main peaks and corresponding intensities: (1): 69 (100); 97 (21); 185 (3) (2): 69 (100); 119 (85); 135 (7) 185 (<1).

$^{19}F$ NMR spectrum (in p.p.m. from $CFCl_3=0$, solvent $CFCl_3$):
(1): +45.3 ($-SO_2F$); -55.4 ($CF_3O-$); -84.4 ($-OCF_2CF_2-$); -112.6 ($-CF_2SO_2F$).
(2): +45.6 ($-SO_2F$); -53.6 ($CF_3O-$); -79.4 ($CF_3$); -127.7 (CF).

Infrared spectrum: main absorption bands (gas, 5 torr): 70:30 mixture of (1) and (2) ($cm^{-1}$): 1473, 1347, 1289, 1262, 1217, 1192, 1165, 807, 608.

EXAMPLE 2

The reaction of example 1 was repeated by operating in like manner, but in the absence of the inert solvent.

In this case, the yield of products (1) and (2) was equal to 60%. The ratio between products (1) and (2) was the same as in example 1.

EXAMPLE 3

Sodium perfluoro-2-methoxyethyl sulphonate (3) and sodium perfluoro-1-methoxyethyl sulphonate (4)

A mixture of products (1) and (2) of example 1, 0.70 mmols, was condensed in a pyrex glass flask equipped with a Teflon valve, containing 50 mg of NaOH, 1 ml of water, 2 ml of ethanol. The closed flask was heated to 70° C. for 16 hours. After evaporation of the liquid in vacuum, the infrared spectroscopy did not reveal the starting products. The conversion of (1) and (2) was complete. A solid product remained in the flask; it was dissolved in methanol and filtered; by evaporation of the methanol there were obtained 190 mg of a white powder; the NMR spectrum was similar to the ones of (1) and (2), but it did not show the signals corresponding to $-SO_2F$.

Characterization of compounds (3) and (4)

$^{19}F$ NMR spectrum (p.p.m. from $CFCl_3=0$, solvent $CH_3OH$): attribution of the signals: (3): -54.8 ($CF_3O-$); -84.3 ($-OCF_2CF_2-$); -117.8 ($-CF_2CF-$ $_2SO_2ONa$); (4): $-52.4$ ($CF_3O$—); $-78.6$ ($CF_3$—); $-133.6$ (CF).

EXAMPLE 4

Perfluoro-2-methoxyethyl sulphonamide (5) and perfluoro-1-methoxyethyl sulphonamide (6)

1.34 mmols of a mixture of products (1) and (2) of example 1, 3.0 mmols of $CFCl_3$ and 2.70 mmols of ammonia were condensed in a pyrex glas flask having a 30 ml volume, and they were allowed to react for 24 hours at room temperature. The rough reaction product was distilled at a pressure of $10^{-3}$ torr through traps maintained at $-50°$ C., $-80°$ C., $-110°$ C., $-196°$ C.

The trap at $-80°$ C. contained 0.30 mmols of products (1) and (2). The traps at $-110°$ C. and $-196°$ C. contained the solvent $CFCl_3$. The residue in the flask was a mixture of (5) and (6), identified by means of NMR analysis, and ammonium fluoride. The residue composed of a mixture of (5) and (6) and of ammonium fluoride was washed with a mixture of $CH_3OH$ (90%) and $CFCl_3$ (10%). The soluble portion, brought to dryness, was a mixture of (5) and (6) identified by means of NMR analysis. The yield, calculated as the ratio between reacted mols of products (1) and (2) and starting mols was of 77%.

Characterization of compounds (5) and (6)

$^{19}F$ NMR spectrum (in p.p.m. from $CFCl_3=0$, solvent $CH_3OH$): attribution of the signals: (5): $-55.4$ ($CF_3O$—); $-84.1$ (—$OCF_2CF_2$—); $-117.9$ (—$CF_2CF_2SO_2NH_2$); (6): $-53.4$ ($CF_3O$—); $-79.1$ ($CF_3$—); $-134.0$ (CF).

EXAMPLE 5

Perfluoro-2-methoxyethyl sulphonic acid (7) and perfluoro-1-methoxyethyl sulphonic acid (8)

310 mg of a mixture of salts (5) and (6) of example 3 were dissolved in 3 ml of sulphoric acid at 96%. It was heated to 160° C. at a pressure of 5 torr, condensing the vapors by means of a distillation head. 210 mg of a colorless hydroscopic liquid were obtained.

Characterization of compounds (7) and (8)

$^{19}F$ NMR spectrum (p.p.m. from $CFCl_3=0$, solvent $D_2O$): attribution of the signals: (7): $-55.3$ ($CF_3O$—); $-85.0$ (—$OCF_2CF_2$—); $-116.3$ (—$CF_2SO_3H$); (8): $-53.0$ ($CF_3O$—); $-79.2$ ($CF_3$—); $-134.2$ (CF).

EXAMPLE 6

Perfluoro 2-ethoxyethyl sulphonyl fluoride (9) and perfluoro 1-ethoxy ethyl sulphonyl fluoride (10)

3.0 mmols of $CF_3C(O)F$ (perfluoroacetyl fluoride) were condensed by means of liquid nitrogen in a steel cylinder of 100 ml of volume and containing 5 g of caesium fluoride, previously molten and ground. There were condensed also 10 mmols of elemental fluorine and the whole was allowed to react at room temperature during 24 hours. At the temperature of liquid nitrogen, unreacted fluorine was removed by evaporation under vacuum. The perfluoroethyl hypofluorite so prepared was transferred into another steel cylinder of 100 ml of volume, containing 3.0 mmols of perfluorovinyl sulphonyl fluoride and 3.0 mmols of $CFCl_3$ solidified in liquid nitrogen. The whole was allowed to reach again the room temperature and after 16 hours the vapors were fractionated through traps maintained at $-55°$ C., $-75°$ C., $-100°$ C. and $-196°$ C.

The trap at $-55°$ C. contained 0.08 mmols of the desired addition products (9) and (10), identified by infrared analysis. The trap at $-75°$ C. contained 1.76 mmols of perfluoro vinyl sulphonyl fluoride and of addition products (9) and (10), like in the preceding fraction. The trap at $-100°$ C. contained 2.74 mmols of perfluoro vinyl sulphonyl fluoride, of addition products (9) and (10) and of $CFCl_3$. The trap at $-196°$ C. contained 3.36 mmols of $CFCl_3$ and $COF_2$ identified by infrared analysis.

The content of the trap at $-75°$ C. and of the trap at $-100°$ C. were furtherly fractionated by means of preparative gas-chromatography and were characterized by NMR spectroscopy.

In this way, 1.6 mmols of perfluorovinyl sulphonyl fluoride, 1.40 mmols of $CFCl_3$, 0.9 mmols of (9), 0.25 mmols of (10) were isolated from the mixture.

EXAMPLE 7

Di(sulphonylfluoride)perfluoropolyether (11)

The starting product (III) of this example had the formula: $OF-CF_2-O(CF_2CF_2O)_m(CF_2O)_n-CF_2-OF$, $m/n=1.62$, an average molecular weight equal to 2160, and was obtained according to European patent 308,905.

These data are useful to calculate the stoichiometry and the yield in the present synthesis example.

6.0 g of the starting product so defined, equivalent to 5.55 mmols of hypofluorite, defined as mmols of hypofluorite = (starting product weight)×2/(average molecular weight), were introduced into a steel cylinder of 30 ml of volume. In the same the cylinder, 8.0 mmols of perfluorovinyl sulphonyl fluoride were condensed. After 48 hours at room temperature, the volatile components of the reaction rough product were distilled at a pressure of $10^{-3}$ torr through traps maintained at $-110°$ C. and $-196°$ C., respectively. The trap at $-110°$ C. contained 3.06 mmols of perfluorovinyl sulphonyl fluoride. The trap at $-196°$ C. contained 0.80 mmols of $COF_2$.

The residue in the cylinder (6.75 g) was identified by NMR spectroscopy as perfluoropolyether functionalized with perfluoroethyl fluorosulphonic groups, wherein end groups OF of the starting product were substituted by perfluoro oxyethyl fluoro sulphonic end groups.

The NMR analysis revealed that these groups were: 1-perfluoroalkoxy 1-perfluoroethyl fluoro-sulphonyl and 2-perfluoroalkoxy 1-perfluoroethyl fluoro-sulphonyl, where perfluoroalkoxy indicates the perfluoropolyethereal chain of the starting product, in a ratio of 29/71 calculated by integration of the corresponding signals $SO_2F$ in the $^{19}F$ NMR.

The yield, calculated as the ratio between the reacted mols of perfluorovinyl sulphonyl and the equivalents, as defined hereinbefore, of hypofluorite in the starting product, was equal to 89%. The obtained perfluoropolyether having a fluorosulphonic functionality, exhibited the following formula:

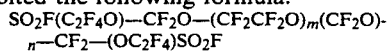
$SO_2F(C_2F_4O)-CF_2O-(CF_2CF_2O)_m(CF_2O)_n-CF_2-(OC_2F_4)SO_2F$ wherein the unit of formula ($OC_2F_4$) was in the isomeric forms indicated for formula (I), $m/n=1.62$, average molecular weight=2,750.

Characterization of product (11)

Average molecular weight = 2,750.

Infrared spectrum: main bands (cm$^{-1}$): 800, 1000, 1350, 1450 (band absent in the starting perfluoropolyether due to functional group —SO$_2$F.

NMR $^{19}$F (no solvent; p.p.m. from CFCl$_3$=0): +46.0 (—CF(CF$_3$)SO$_2$F); +45.2 (—CF$_2$CF$_2$SO$_2$F); 51.5 −53.0 and −55.0 (OCF$_2$O—); −79.2(—CF(CF$_3$)SO$_2$F; −83.8 (—OCF$_2$CF$_2$SO$_2$F); −88.9 −90.6 (—OCF$_2$CF$_2$O—); −112.5 (—OCF$_2$CF$_2$SO$_2$F); −127.5 (—CF(CF$_3$)SO$_2$F).

EXAMPLE 8

Di(sodium sulphonate)perfluoropolyether (12)

To the sulphonyl fluoride of example 7, suspended in water under stirring, aqueous sodium hydroxide 2N was added. An emulsion immediately formed and the addition of sodium hydroxide solution was continued until the emulsion remained basic on check by means of an indicator paper. It was heated to 100° C. for 2 hours in order to surely obtain a complete hydrolysis of the SO$_2$F groups; subsequently, water was removed by evaporation under vacuum. The residue was a solid product exhibiting a wax-like consistency which, other than the starting sulphonyl fluoride, was soluble in acetone.

The $^{19}$F NMR spectrum of the acetone solution of the above-mentioned product did no longer exhibit the signals due to the —SO$_2$F groups.

Obtained was a perfluoropolyethereal product with salified sulphonic end groups of formula:

NaO.O$_2$S(C$_2$F$_4$O)—CF$_2$O—(CF$_2$CF$_2$O)$_m$(CF$_2$O)$_n$—CF$_2$—(OC$_2$F$_4$)SO$_2$.ONa where the unit of formula (OC$_2$F$_4$) was in the isomeric forms indicated for formula (I), m/n=1.62, average molecular weight = 2,780 (Product 12).

NMR $^{19}$F in p.p.m. from CFCl$_3$=0 (solvent acetone): −51.0 −54.6 and −56,3 (—OCF$_2$—); −78.8 (—CF(CF$_3$)—SO$_2$ONa); −83.9 (—OCF$_2$CF$_2$SO$_2$ONa); −88.6 and −90.2 (—OCF$_2$CF$_2$O—); −116.0 (—OCF(CF$_3$)SO$_2$ONa).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A process for preparing perfluoroalkoxysulphonic compounds having formula:

$$R_f(-OC_2F_4-SO_2X)_p \quad (I)$$

in which:

p represents 1 or 2;

X represents F;

R$_f$, for p=1, represents a perfluoroalkyl group containing 1 to 6 carbon atoms or a perfluoroethereal chain having formula

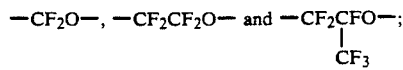

in which:

R$_3$ represents a perfluoroalkyl group containing 1 to 3 carbon atoms;

R$_4$O represents a perfluorooxyalkylene group selected from

D represents —F or —CF$_3$, k represents 0 or an integer from 1 to 100 included, and when k is equal to or greater than 2, at least two of the above said perfluorooxyalkylene groups can be simultaneously present according to a random distribution of the combinations thereof;

q represents 0 or 1; and for p=2, R$_f$ represents a perfluoroalkylene chain containing 2 to 6 carbon atoms or a perfluoroethereal chain having formula:

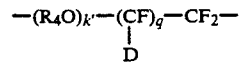

in which R$_4$O, D and q are the same as defined before and k' represents an integer from 1 to 100; said process comprising a perfluorovinylsulphonyl fluoride of formula (II):

$$CF_2=CF-SO_2F \quad (II)$$

being reacted with a hyprofluorite of formula (III):

$$R_f(OF)_r \quad (III)$$

in which R$_f$ is the same as defined hereinbefore, and r represents 1 or 2, optionally in an inert solvent, at a temperature ranging from −140° C. to +40° C.

2. The process according to claim 1, wherein it is operated in an inert organic solvent selected from the group consisting of straight or cyclic fluorocarbons, chlorofluorocarbons, perfluoroamines and perfluoroalkylethers, or mixtures thereof.

3. The process according to claim 2, wherein the solvent is selected from the group consisting of 1,1,1-trifluoro-trichloroethane, CFCl$_3$, CF$_2$Cl$_2$, c.C$_4$F$_8$, c.C$_6$F$_{12}$, 1-chloropentafluoroethane, 1,1,2-trichloro-1,2,2-trifluoroethane, 1,2-dichlorotetrafluoroethane, or mixtures thereof.

4. The process according to claim 1, wherein it is conducted at a temperature ranging from −100° C. to 0° C.

5. The process according to claim 1, wherein R$_f$ in formula (III) consists of a perfluoroethereal chain of formula:

$$-CF_2-O-(CF_2CF_2O)_m(CF_2O)_n-CF_2-$$

in which m and n represent integers from 1 to 100, and m+n≦100, the perfluorooxyalkylene units being randomly distributed along the chain.

6. The process according to claim 1, wherein in formula (I)

(OC$_2$F$_4$—SO$_2$X)

can be

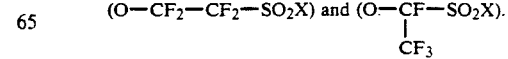

* * * * *